United States Patent
Lu et al.

(12) 
(10) Patent No.: US 6,303,646 B1
(45) Date of Patent: Oct. 16, 2001

(54) CANCER TREATMENT WITH GÖ 6976

(76) Inventors: Zhimin Lu, 10172 Black Mountain Rd., Apt. 103, San Diego, CA (US) 92126; Keming Wang, 79 East Ximei Street, Apt. 303, Suzhou (CN), 215002

( * ) Notice: Subject to any disclaimer, the term of this patent is extended or adjusted under 35 U.S.C. 154(b) by 0 days.

(21) Appl. No.: 09/370,190

(22) Filed: Aug. 9, 1999

(51) Int. Cl.⁷ .................................................. A61K 31/40
(52) U.S. Cl. ................................................ 514/410
(58) Field of Search ............................................ 514/410

(56) References Cited

U.S. PATENT DOCUMENTS

| | | | |
|---|---|---|---|
| 5,489,608 | * 2/1996 | Kleinschroth et al. | 514/410 |
| 5,723,456 | 3/1998 | Jirousek | 514/183 |
| 5,744,460 | 4/1998 | Muller | 514/44 |
| 5,821,072 | 10/1998 | Schwartz | 435/15 |
| 5,843,935 | 12/1998 | Heath, Jr. | 514/183 |
| 5,882,927 | 3/1999 | Bennett | 435/375 |
| 5,885,970 | 3/1999 | Bennett | 514/44 |

\* cited by examiner

*Primary Examiner*—Jerome D. Goldberg
(74) *Attorney, Agent, or Firm*—John R. Ross; John R. Ross, III (57) ABSTRACT

A chemotheraputic cancer treatment in which Gö6976 or one of its derivatives is administered to a mammal for the treatment of the cancer. The Gö6976 or its derivative is directed to PKC α activity. Experiments have shown Gö6976 to be effective for the treatment of breast cancer, leukemia, lung cancer, bone cancer and skin cancer. These treatments may be accomplished utilizing Gö6976 or its derivatives alone or in combination with other prior art chemotherapy agents or in combination with radiation therapy. In a preferred embodiment Gö6976 is used for the treatment of cancer as a preventative drug by preventing cancer cell formation.

14 Claims, 7 Drawing Sheets

CANCER TREATMENT WITH GÖ 6976

This invention relates to cancer treatments and especially to cancer treatments directed to protein kinase C α enzyme.

BACKGROUND OF THE INVENTION

Researchers have recognized that a family of enzymes known as protein kinase C enzymes is associated with a large number of cancers. This family includes at least eleven isoenzymes. A particular member of this family is identified as the protein kinase C alpha enzyme, abbreviated: PKC α.

Researches have reported increases in PKC α activity in human breast tumors (NG et al., *Science.* 283:2085–2089) and significant increases in PKC α expression in prostate cancers (Cornford et al., *Am. J. Pathol.* 154: 137–144). Researchers have reported that PKC α is required for the metastasis of human melanoma (Dennis et al., *Cancer Lett.* 128:65–70) and that PKC α is related to the progression of brain tumors (Shen et al., *Mol. Pharmacol.* 55:396–402). There is general agreement among many cancer researchers that some of the most dangerous cancers can be treated with chemotheraputic agents or specially designed oligonuclotides targeted to PKC α.

Recently, Muller et al were granted a patent, U.S. Pat. No. 5,744,460, which discloses a cancer treatment utilizing an antisense oligonucleotide targeted to PKC α combined with a chemotherapeutic agent. U.S. Pat. Nos. 5,882,927 and 5,885,970 issued to Bennett et al also disclose antisense oligonuclotides targeted to PKC. Several patents that disclose PKC α inhibitors for treating cancers have been issued to Heath, Jr., et al. These include U.S. Pat. No. 5,843,935. U.S. Pat. No. 5,723,456 is another example of a cancer treatment in which a PKC directed emzyme is proposed as a method to treat cancer. U.S. Pat. No. 5,821,072 granted to Schwartz, et al proposes the use of certain chemotherapeutic agents to attempt to reduce PKC activity. The disclosures of the above listed patents are incorporated herein by reference.

Figure 1:
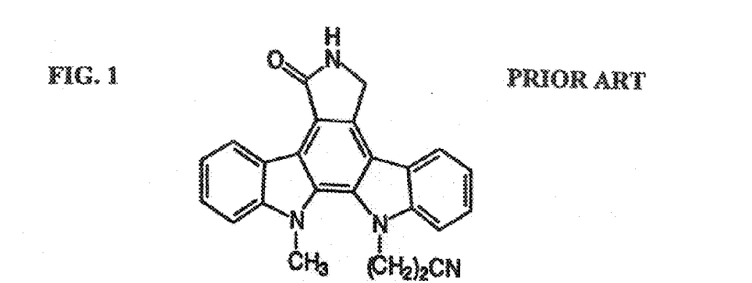
FIG. 1 is chart showing the chemical structure of Gö6976.

A chemical known as Gö6976, available from Calbiochem Corp. and Alexis Corp. (both with offices in San Diego, Calif.), is known to be an inhibitor of PKC α. G ö6976 is designated as C24H18N40 and a diagram of the molecule is presented in FIG. 1. Applicant et al reported in Molecular Cellular Biology, 17:3418–3428 based on a variety of experiments that Gö6976 prevented TPA-induced downregulation of the of PKC α and is a more specific inhibitor for PKC α.

What is needed is a better treatment for cancer.

SUMMARY OF THE INVENTION

The present invention provides a chemotheraputic cancer treatment in which Gö6976 or one of its derivatives is administered to a mammal for the treatment of the cancer. The Gö6976 or its derivative is directed to PKC α activity. Experiments have shown Gö6976 to be effective for the treatment of breast cancer, leukemia, lung cancer, bone cancer and skin cancer. These treatments may be accomplished utilizing Gö6976 or its derivatives alone or in combination with prior art chemotherapy agents or with radiation therapy. In a preferred embodiment Gö6976 is used for the treatment of cancer as a preventative drug by preventing cancer cell formation.

DETAILED DESCRIPTION OF PREFERRED EMBODIMENTS

The present invention may be described by reference to the figures. Several varieties of cancer cells were grown in laboratory conditions and tested with Gö6976 and the results recorded. The experiments and the results are described below.

EXPERIMENTS

Cell Culture

Cell cultures used the following cancer cells, which were supplied from the American Type Culture Collection, Rockville, Md.:

MDA-MB-468 human breast cancer cells,

MDA-MB-453 human breast cancer cells,

A431 human epidermoid carcinoma cells,

U-2 OS human osteosacoma cells,

3Y1 rat fibroblast cells overexpressing the epidermal growth factor receptor (EGFR).

These cells were maintained in Dulbecco's modified Eagle medium (DMEM) supplemented with 10 percent bovine calf serum.)

Small cell lung cancer cells (NCI-H1048),

Non-small cell lung cancer cells (NCI-H2342).

Small cell lung cancer cells were grown in RPMI 1640 medium with 2 mM L-glutamine adjusted to contain 1.5 g/L sodium bicarbonate, 4.5 g/L glucose, 10 mM HEPES, 1.0 mM sodium pyruvate, and 5% fetal bovine serum. Non-small cell lung cancer cells were grown in RPMI 1640 medium supplemented with 5% fetal bovine serum, 5 ug/ml insulin, 10 ug/ml transferrin, 30 nM sodium selenite, 10 nM hydrocortisone, 10 nM beta-estradiol, 10 mM HEPES, and 2 mM L- glutamine.

HL60 human acute promyelocytic leukemia cells were grown in RPMI 1640 medium containing 10 percent heat-inactivated fetal bovine serum (FBS).

For growth of these cells in soft agar, $1\times10^3$ cells were suspended in top agar (consisting of 20 percent calf serum, 0.38 percent agar and the remainder DMEM) and overlaid onto hardened bottom agar (DMEM, 20 percent calf serum and 0.7 percent agar) as reported by Qureshi et al., in *Biochem. Biophys. Res. Commun.* 192:969–975.

Materials

Gö6976 was obtained from Calbiochem.

Cell Viability Assay

Cells were seeded for 24 hours. Then they were either treated with Gö6976 or left untreated. The cells were then collected periodically and evaluated using trypan blue dye exclusion to asses viability using the method described by CY Chen, et al, in J.Biol. Chem. 273:16700–16709.

Experimental Results

Breast Cancer

Figure 2:
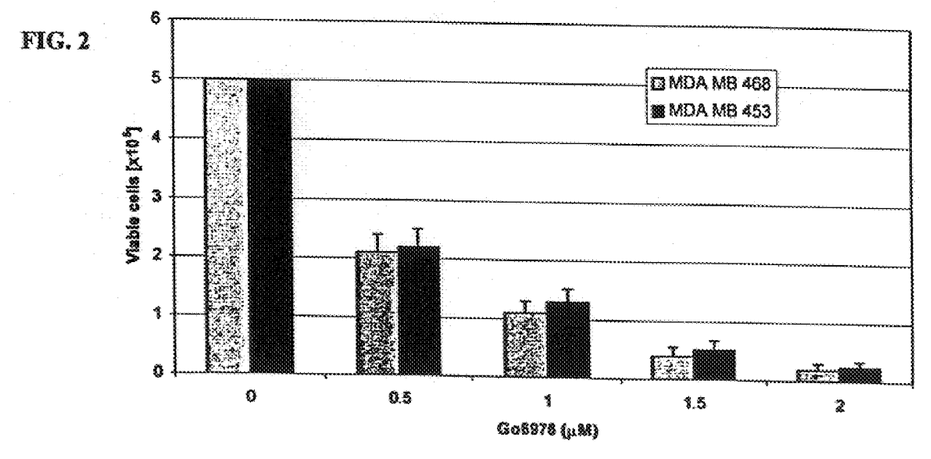
FIGS. 2 through 8 are graphs showing the results of treating various cancer cells with Gö6976.
Figure 3:
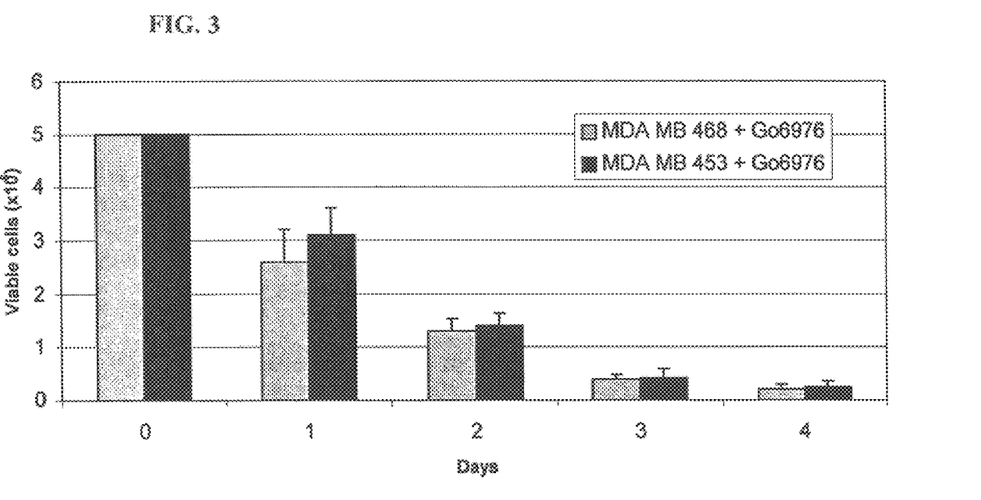

The results of treatment of human breast cancer cells (MDA-MB-468 and MDA-MB-453 with Gö6976 are shown in FIGS. 2 and 3. Cultures containing about $5\times10^5$ cells were treated with 0.0, 0.5, 1.0 and 2.0 micromole of Gö6976 and the viable cells were counted at day 4. As shown in FIG. 2 cell count was reduced to about $1\times10^5$ when treated with 1 micromole of Gö6976 and to less than $0.3\times10^5$ when treated with 2.0 micromolar of Gö6976. In a separate experiment as shown in FIG. 3, the breast cancer cells were treated with 2.0 micromoles of Gö6976 and measurements made at 24 hours intervals for 4 days. Viable cell concentration appears to be reduced by approximately half each 24 hours. In both FIG. 2 and FIG. 3 error bars indicated the estimated standard error based on three independent experiments.

Leukemia

Figure 4:
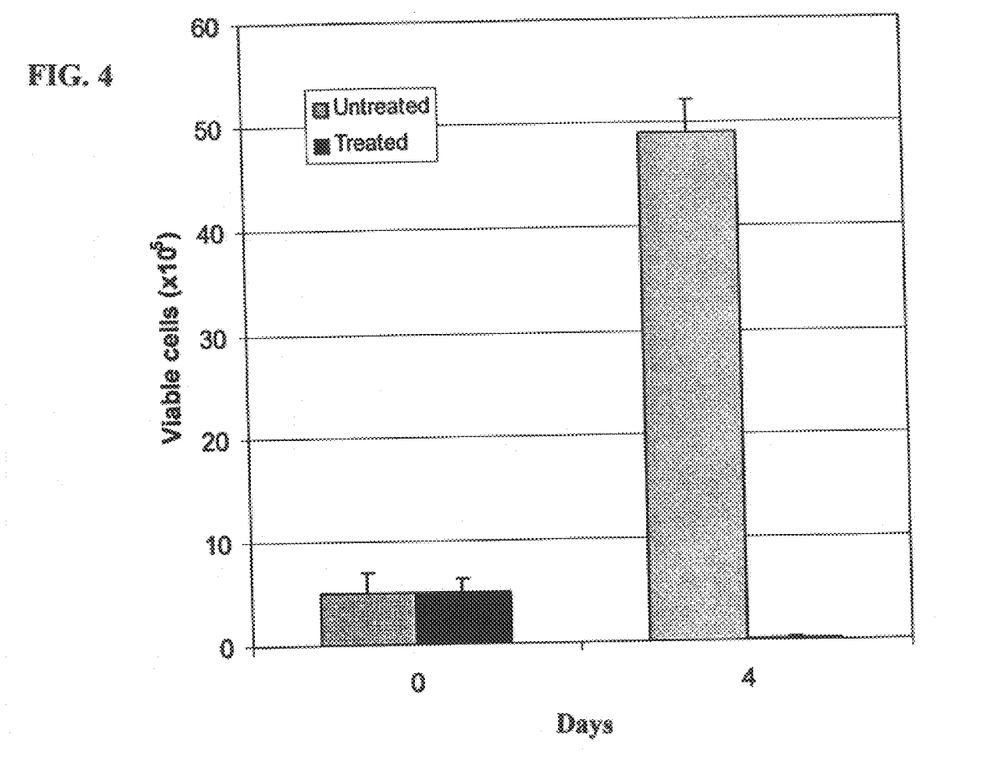

The results of treatment of HL60 acute promyelocytic leukemia cells with Gö6976 are shown in FIG. 4. One of two samples of $5\times10^5$ cells was treated with 2 micromoles of Gö6976 and the viable cells were counted after four days. At four days the cells in the untreated sample had grown by a factor of nearly 10 to almost $5\times10^6$ cells whereas viable cells in the treated sample was less than $0.2\times10^5$.

Lung Cancer

Figure 5:
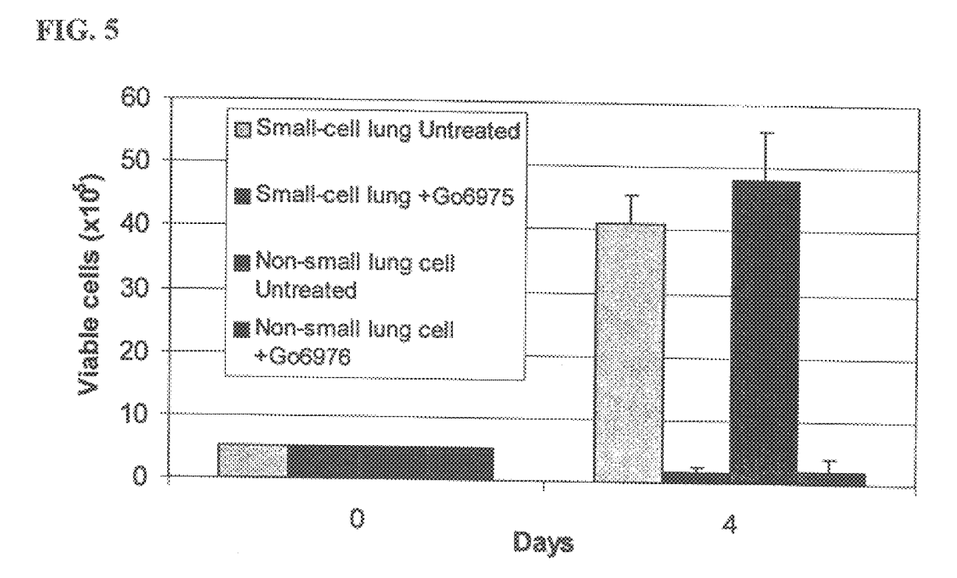

The results of treatment of lung cancer cells are shown in FIG. 5. Two samples each of about $5\times10^5$ cells small lung cancer cells and non-small lung cancer cells were prepared and one sample of each type was treated with Gö6976 and the viable cells were counted at day 4. In the untreated samples the cancer cells had multiplied by almost a factor of 10 and in the treated samples the count had decreased to less than 0.5 of the original count.

Bone Cancer

Figure 6:
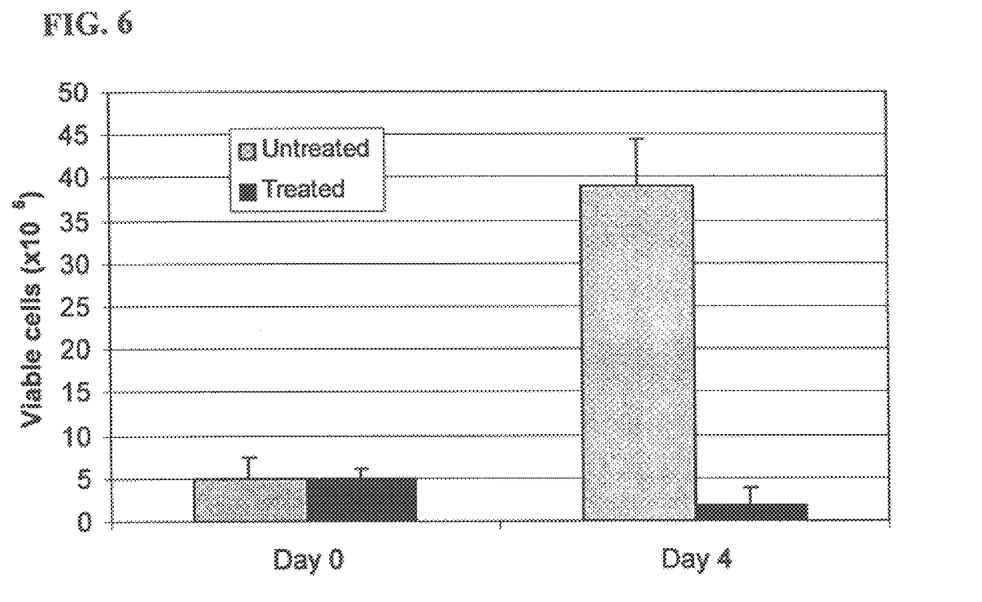

The results of treatment of osteosarcoma cells are shown in FIG. 6. One of two samples of about $5\times10^5$ cells was treated with 2 micromoles of Gö6976 and the viable cells were counted after four days. At four days the cells in the untreated sample had grown by a factor of nearly 8 to almost $4\times10^6$ cells whereas viable cells in the treated sample were reduced to about half the original count.

Skin Cancer

Figure 7:
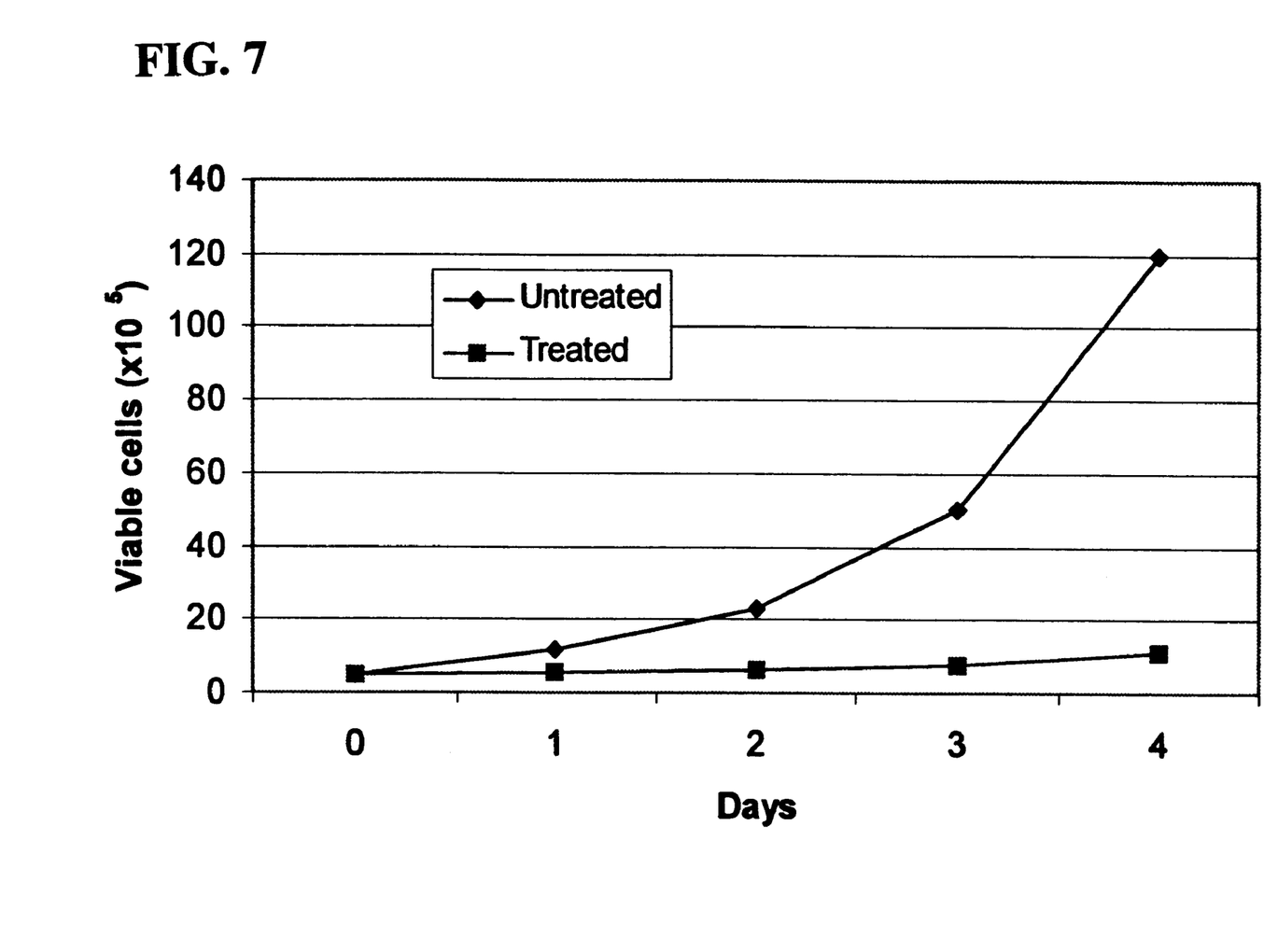

The results of treatment of A431 human epidermoid carcinoma cells are shown in FIG. 7. One of two samples of about $5\times10^5$ cells was treated with 2 micromoles of Gö6976 and the viable cells were counted each 24 hours for four days. At four days the cells in the untreated sample had grown by a factor of about 24 to almost $1.2\times10^7$ cells whereas viable cells in the treated sample had approximately doubled.

EGF Induced Cell Transformation

Figure 8:
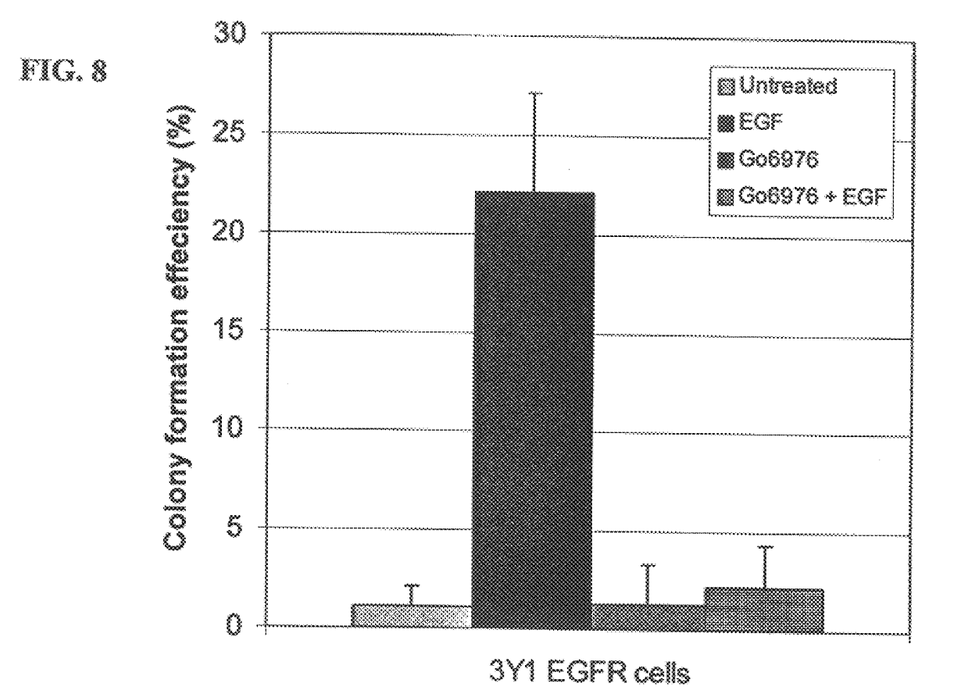

FIG. 8 shows the effect of Gö6976 for blocking cell transformation caused by epidermal growth factor (EGF). 3Y1 cells overexpressing EGF receptors showed a transformed morphology upon 100 nanamoles EGF treatment for 24 hours. Co-treatment with 250 nanamoles Gö6976 and EGF completely blocked EGF-induced cell transformation while treatment with Gö6976 alone did not show any toxic effect on 3Y1 EGFR cells.

The effect of Gö6976 on blocking EGF-induced cell transformation was further confirmed by checking anchorage-independent cell growth. As shown in FIG. 8, cultures of $1\times10^3$ 3Y1 cells overexpressing EGF receptors were prepared by suspending the cells in soft agar. One sample was left untreated, one was treated with 100 nanomoles of EGF, one sample was treated with 100 nanamoles of EGF and 250 nanamoles of Gö6976 and one sample was treated with 250 nanaomoles of Gö6976. In each case the percentage of cell forming colonies were determined three weeks after suspending the cells in soft agar. Colony forming efficiency of EGF was greatly reduced by Gö6976.

No Significant Effect on Normal Cells

Applicant tested Gö6976 on normal cells including rat 3Y1 fibroblast in the concentrations used in the above-described experiments and no significant toxic effects on the cells were noted. Toxic effects begin to show up at concentrations of about 5 micromoles in these types of cells.

Human and Animal Treatment

The above described test show clearly that Gö6976 has a strong apototic effect on a variety of human cancer cells and that it can inhibit growth of other human cancer cells. Based on the EGF experiments showing a blocking of the effects of the EGF induced cell transformation, Gö6976 also can be used as a cancer preventive reagent. The lack of toxic effects on normal cells at the concentrations needed for effectiveness against the cancer cells shows that Gö6976 is very valuable chemotheraputic agent. It could be applied in many of the well-known methods currently used for chemotheraputic treatment. For example, it may be injected directly into tumors, injected into the blood stream or taken orally or applied through the skin with patches. The dose chosen should be sufficient to constitute effective treatment but not so high as to cause unacceptable side effects. The state of the cancer and the health of the patient should preferably be closely monitored during and for a reasonable period after treatment.

While the above examples describe the effectiveness of Gö6976 as a chemotheraputic treatment for various cancers they are not intended as a limitation of the invention. The chemical was effective in killing or reducing the growth rate of all cancer cells tested. Therefore, it should be obvious that it would be effective as a treatment to cancer cells not tested that are associated with increased levels of PKC α expression and/or activity such as prostate cancer, pancreatic cancer and melanoma. Derivatives of Gö6976 that are effective in inhibiting PKC α should also be effective as a cancer treatment. Also, since Gö6976 prevents cell transformation it should also work as a preventative drug, especially for people having a high risk for particular cancers.

What is claimed is:

1. A method of treating a cancer, consisting of breast cancer, leukemia, lung cancer, bone cancer, skin cancer, prostate cancer, melanoma or pancreatic cancer, in a mammal comprising administering to said mammal a chemical targeted to PKC α and monitoring said mammal to determine state of said cancer, wherein said chemical is Go6976 and it is administered in doses large enough to be effective in treating said cancer.

2. A method as in claim 1 wherein said mammal is a human.

3. A method as in claim 2 wherein said cancer is breast cancer.

4. A method as in claim 2 wherein said cancer is leukemia.

5. A method as in claim 2 wherein said cancer is lung cancer.

6. A method as in claim 2 wherein said cancer is bone cancer.

7. A method as in claim 2 wherein said cancer is skin cancer.

8. A method as in claim 2 wherein said cancer is prostate cancer.

9. A method as in claim 2 wherein said cancer is melanoma.

10. A method as in claim 2 wherein said cancer is pancreatic cancer.

11. A method as in claim 1 wherein said chemical is administered by injecting it directly into a tumor.

12. A method as in claim 1 wherein said chemical is administered by injecting it into said mammal's blood stream.

13. A method as in claim 1 wherein said chemical is administered orally.

14. A method as in claim 1 wherein said chemical is administered through said mammal's skin.

* * * * *